United States Patent
Défossez et al.

(10) Patent No.: US 11,523,854 B2
(45) Date of Patent: Dec. 13, 2022

(54) DRIVER AND SYSTEM FOR THREADED INTRAMEDULLARY NAIL RETAINING ENDCAPS

(71) Applicant: DEPUY SYNTHES PRODUCTS, INC., Raynham, MA (US)

(72) Inventors: Henri Défossez, Neuchatel (CH); Gregor Spreiter, Solothurn (CH); Simon Wampfler, Lohn-Ammannsegg (CH); Simon Scherrer, Zurich (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 406 days.

(21) Appl. No.: 16/569,122

(22) Filed: Sep. 12, 2019

(65) Prior Publication Data
US 2021/0077172 A1    Mar. 18, 2021

(51) Int. Cl.
| A61B 17/92 | (2006.01) |
| A61B 17/72 | (2006.01) |
| A61B 17/00 | (2006.01) |
| A61B 17/90 | (2006.01) |

(52) U.S. Cl.
CPC ............ *A61B 17/921* (2013.01); *A61B 17/72* (2013.01); *A61B 17/90* (2021.08); *A61B 2017/00424* (2013.01); *A61B 2017/00477* (2013.01); *A61B 2017/00862* (2013.01)

(58) Field of Classification Search
CPC .................................................. A61B 17/921
See application file for complete search history.

(56) References Cited

U.S. PATENT DOCUMENTS

| 2,406,952 | A | * | 9/1946 | Anatol | .................... | B25B 15/02 |
| | | | | | | 81/452 |
| 3,438,413 | A | * | 4/1969 | Borah | .................... | B25G 1/105 |
| | | | | | | 81/177.1 |
| 6,033,405 | A | * | 3/2000 | Winslow | ............... | A61F 2/4601 |
| | | | | | | 606/86 R |
| 6,053,922 | A | * | 4/2000 | Krause | ................. | A61B 17/164 |
| | | | | | | 464/78 |
| 2005/0273102 | A1 | * | 12/2005 | Powell | ................. | A61B 17/921 |
| | | | | | | 606/62 |

(Continued)

FOREIGN PATENT DOCUMENTS

EP         2 756 822 A2    7/2014

*Primary Examiner* — Zade Coley
(74) *Attorney, Agent, or Firm* — Fay Kaplun & Marcin, LLP

(57) ABSTRACT

A driver for engaging an endcap of an intramedullary nail. The driver includes a handle extending along a longitudinal axis of the driver from a proximal end to a distal end. The handle having a handle channel extending longitudinally therethrough. The driver also includes a shaft extending through the handle channel from a proximal end to a distal end along the longitudinal axis. The shaft having a shaft channel extending longitudinally therethrough. The distal end of the shaft extends distally from the handle. The distal end of the shaft forms a driving element to be inserted into a head portion of the endcap. The driver further includes a retention pin slidably received in the shaft channel. The retention pin extends also extends along the longitudinal axis. The distal end of the retention pin is configured to reversibly lock the shaft to the head portion of the endcap.

16 Claims, 8 Drawing Sheets

(56) References Cited

U.S. PATENT DOCUMENTS

| | | | | |
|---|---|---|---|---|
| 2011/0060336 A1* | 3/2011 | Pool | ............... | A61B 17/7216 |
| | | | | 606/57 |
| 2012/0065638 A1* | 3/2012 | Moore | ............... | A61B 17/7225 |
| | | | | 606/62 |
| 2012/0283739 A1* | 11/2012 | Ralph | ............... | A61B 17/92 |
| | | | | 606/99 |
| 2013/0268010 A1* | 10/2013 | Santangelo | ............... | A61B 17/8888 |
| | | | | 606/304 |
| 2015/0374418 A1* | 12/2015 | Martin | ............... | A61B 17/7074 |
| | | | | 606/291 |
| 2017/0112552 A1* | 4/2017 | Sinnott | ............... | A61B 17/1655 |
| 2017/0367748 A1 | 12/2017 | Plotkin | | |
| 2018/0049753 A1* | 2/2018 | Chenaux | ............... | A61B 50/30 |
| 2018/0214190 A1* | 8/2018 | Erramilli | ............... | A61B 17/7082 |
| 2019/0000509 A1* | 1/2019 | Cowens | ............... | A61B 17/68 |

* cited by examiner

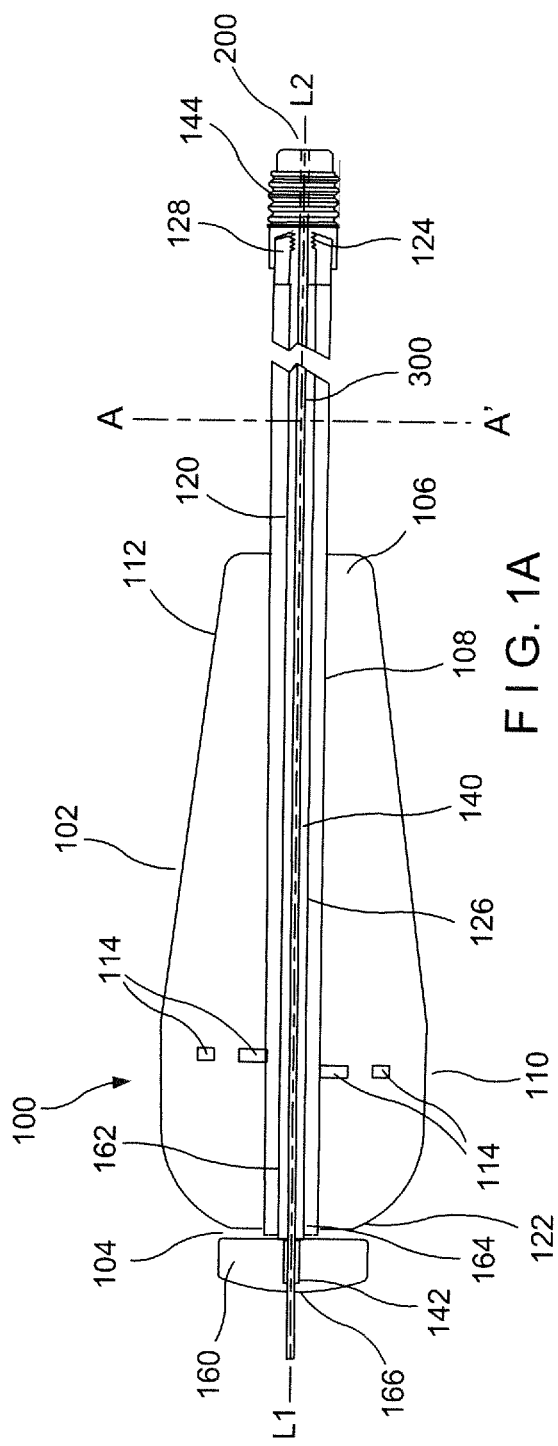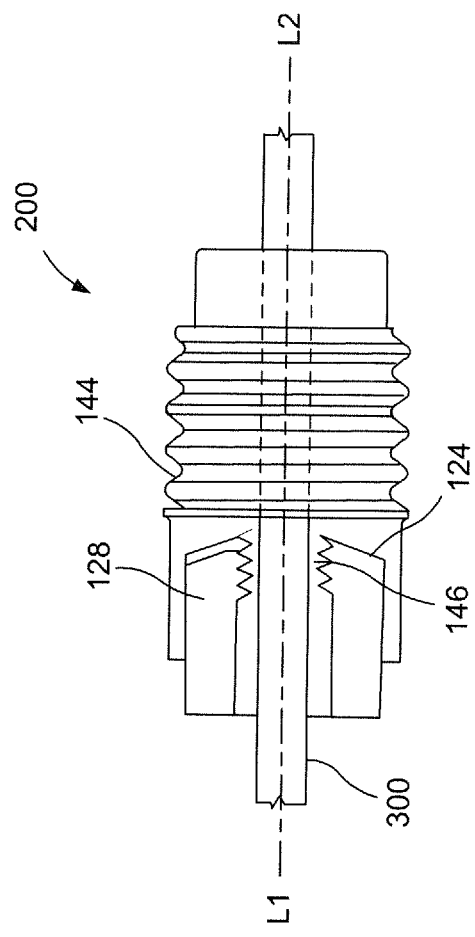

DRIVER AND SYSTEM FOR THREADED INTRAMEDULLARY NAIL RETAINING ENDCAPS

FIELD OF INVENTION

The present invention relates generally to a driver and a system for fixation of two or more parts of a fractured bone. More specifically, the present invention relates to a driver and a system for engaging an endcap for insertion into a channel of an intramedullary nail for internal fixation of a long bone, such as a femur.

BACKGROUND

Fractures of the femur often occur in the femoral neck and intertrochanteric regions. Such fractures may be treated with screws or other fixation devices inserted into or through a bone to stabilize and fix the positioning of different portions of the bone relative to one another after they have been placed into corrective alignment. Trochanteric bone fixation treatments often comprise the insertion of an intramedullary nail into a medullary cavity of a bone and the subsequent insertion of a bone fixation nail into a condylar portion of the bone at an angle relative to the intramedullary nail (i.e., along an axis of the trochanter).

SUMMARY OF THE INVENTION

One exemplary embodiment of the present application is a driver for engaging an endcap of an intramedullary nail. The driver comprises a handle extending along a longitudinal axis of the driver from a proximal end to a distal end and having a handle channel extending longitudinally therethrough. The driver comprises a shaft extending through the handle channel from a proximal end to a distal end along the longitudinal axis having a shaft channel extending longitudinally therethrough. The distal end of the shaft extends distally from the handle. The distal end of the shaft forms a driving element configured to be inserted into a head portion of the endcap. The driver further comprises a retention pin slidably received in the shaft channel and extending from a proximal end to a distal end along the longitudinal axis. The distal end of the retention pin is configured to reversibly lock the shaft to the head portion of the endcap.

In another aspect of the present application, a system for engaging a proximal end of an intramedullary nail is provided. The system comprises a driver having a handle extending along a longitudinal axis of the driver from a proximal end to a distal end and having a handle channel extending longitudinally therethrough. The driver also includes a shaft extending through the handle channel from a proximal end to a distal end along the longitudinal axis having a shaft channel extending longitudinally therethough. The distal end of the shaft extends distally from the handle. The distal end of the shaft forms a driving element. The driver further includes a retention pin slidably received in the shaft channel and extending from a proximal end to a distal end along the longitudinal axis. The distal end of the retention pin comprises threading. The retention pin also includes a lumen extending longitudinally therethrough. The system also comprises an endcap having a lumen extending therethrough. The end cap comprises a body configured to engage a channel of the intramedullary nail, and a head portion configured to receive the driving element therein and to reversibly lock the head portion to the shaft. The head portion of the end cap comprises threading configured to threadedly engage a corresponding threading of the retaining pin. The system further comprises a guidewire slidably inserted through the lumen of the retention pin and the lumen of the endcap to align the driving element to the head portion of the endcap.

These and other aspects of the invention will become apparent to those skilled in the art after a reading of the following detailed description of the invention, including the figures and appended claims.

BRIEF DESCRIPTION OF THE FIGURES

FIG. 1a shows a driver according to an embodiment of the present invention for engaging an endcap for inserting into a channel of an intramedullary nail.

FIG. 1b shows a side view of the handle of the driver of FIG. 1a.

FIG. 1c shows another side view of the handle of the driver of FIG. 1a.

FIG. 2 shows a detailed view of a distal most portion of the driver of FIG. 1a engaging an endcap for inserting into a channel of an intramedullary nail.

DETAILED DESCRIPTION

Figure 1B:
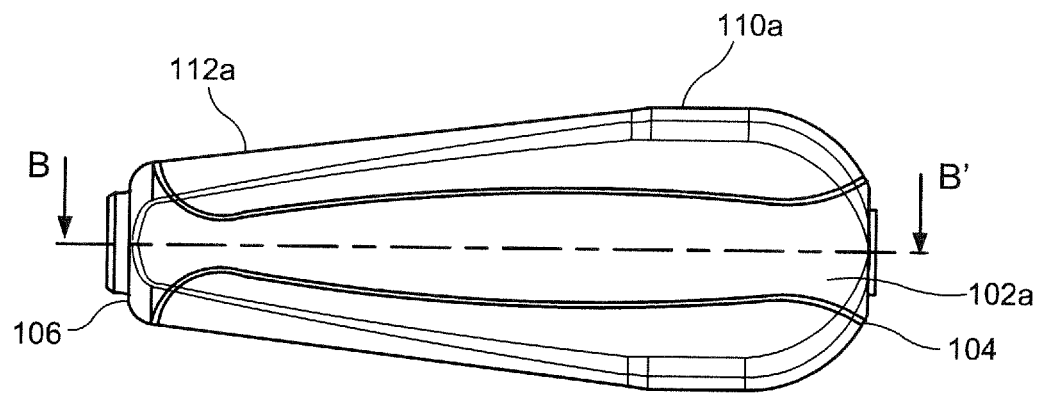

The present disclosure may be further understood with reference to the following description and the appended drawings, wherein like elements are referred to with the same reference numerals. It should be noted that the terms "proximal" and "distal," as used herein are intended to refer to a direction toward (proximal) and away from (distal) a user of the device.

FIGS. 1a-c and 3 shows a driver 100 for engaging an endcap 200 couplable to a proximal end 12 of an intramedullary nail 10. The driver 100 includes a handle 102 extending along a longitudinal axis L1 from a proximal end 104 to a distal end 106. The handle 102 has a handle channel 108 that extends longitudinally from the proximal end 104 to the distal end 106 through the handle 102 along the longitudinal axis L1. The handle 102 may have any suitable size and shape for being held within the palm of a user's hand to manually manipulate the handle 102. Preferably, the handle 102 is suitably sized and shape to provide an ergonomic shape for a user to hold within the palm of his hand and to rotate the driver 100 by hand.

In an exemplary embodiment, the handle 102 has an elongated shape. As shown in FIG. 1a, the handle 102 has an elongated shape that is tapered such that a diameter of the handle 102 is reduced from an enlarged portion 110 (located proximal to the distal end 106) to the distal end 106. In particular, the handle 102 has a bulb shape. Specifically, the handle 102 increases from a first diameter at the proximal end 104 to a maximum diameter at the enlarged portion 110 and includes a tapered portion 112 adjacent the distal end 106, the tapered portion 112 being formed to aid in ergonomic use of the handle 102 in a hand of a user.

The driver 100 also includes a shaft 120 that extends through the handle channel 108 from a proximal end 122 to a distal end 124 along the longitudinal axis L1. The shaft 120 is co-axial with the handle 102 along the longitudinal axis L1. In some embodiments, the shaft 120 has a cross-sectional diameter from about 7.5 mm to about 14 mm in a plane orthogonal to the longitudinal axis L1 between the proximal end 122 and a portion proximal to a driving element 128 located at the distal end 124 (e.g., along a plane A-A' as shown in FIG. 1a). The shaft 120 has a shaft channel 126 extending longitudinally from the proximal end 122 to the distal end 124 through the shaft 120 along the longitudinal axis L1. The shaft channel 126 is co-axial with the shaft 120 and defines an inner diameter of an interior surface of the shaft channel 126. In some embodiments, the inner diameter of the shaft 120 is from about 4.15 mm to about 4.5 mm. As shown in FIG. 1a, the shaft 120 is longer than the handle 102 such that the distal end 124 of the shaft 120 extends distally further than the distal end 106 of the handle 102. For example, the shaft 120 extends from about 166 cm to about 328 cm, distally further than the distal end 106 of the handle. The proximal end 122 of the shaft 120 may be fixed anywhere along a length of the handle channel 108. For example, as shown in FIG. 1a, the proximal end 122 of the shaft 120 is positioned at the proximal end 104 of the handle 102. In another example, the proximal end 122 of the shaft 120 is positioned within the handle channel 108, between the proximal and distal ends 104, 106 of the handle 102.

Figure 1D:
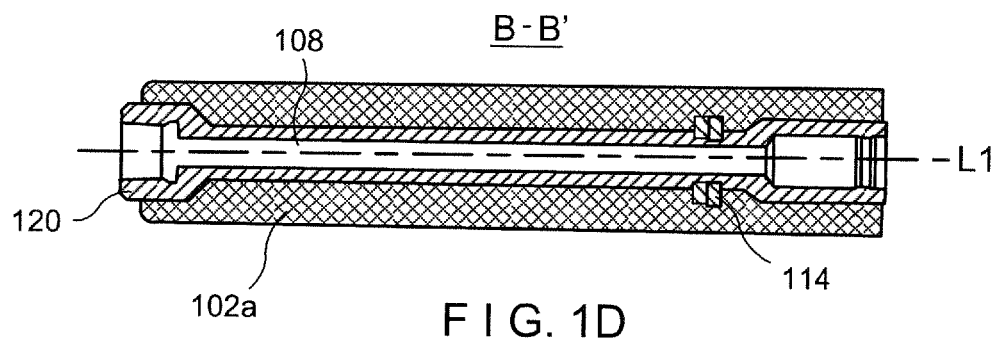
FIG. 1d shows a cross-sectional view of the handle shown in FIGS. 1b and 1e.
Figure 1C:
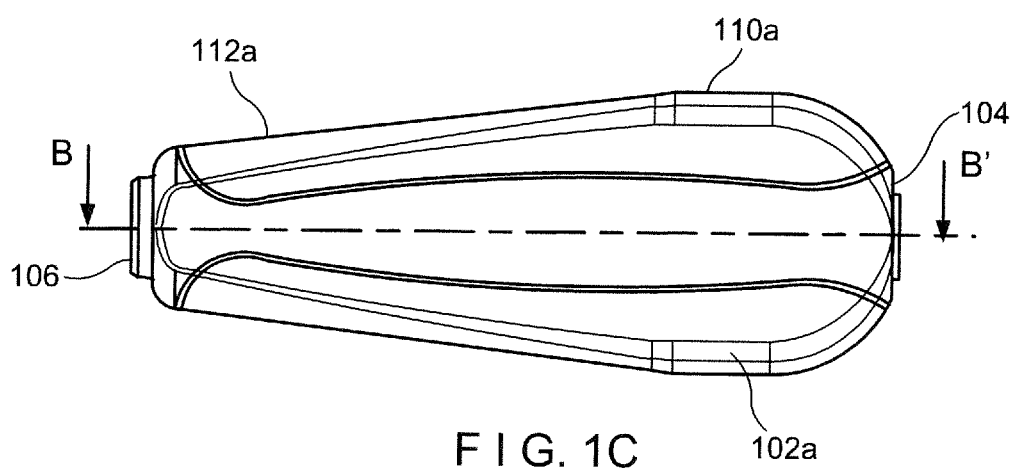

In one embodiment, the handle 102a may be formed as an elastomeric (e.g., silicone) molding over the shaft 120, for example, as shown in FIGS. 1b-1d. The elastomeric molding is formed over the shaft 120 such that a handle channel 108 is defined therein around the shaft 120. The elastomeric molding provides a soft material that reversibly deforms to provide an ergonomic shape for a user to hold within the palm of his hand. In addition, the elastomeric molding increases friction between the surface of the handle 102a and the palm of the user's hand to provide a handle 102a that is easy and comfortable to hold in the hand of the user. FIG. 1b shows a side view of an elastomeric molded handle 102a over a portion of a shaft 120, and FIG. 1c shows a side view of the elastomeric molded handle 102a from a side opposite that shown in FIG. 1b. As can be seen in FIGS. 1b and 1c, the handle 102a is molded over the shaft 120 in a tapered shape where a width of the handle 102 increase from a first diameter at the proximal end 104 to a maximum width at an enlarged portion 110a of the handle 102a and includes a tapered portion 112a having a narrower width adjacent the distal end 106. FIG. 1d shows a cross-sectional view of the embodiment of FIGS. 1b and 1c along a plane along the longitudinal axis L1 (e.g., along a plane B-B' as shown in FIG. 1b). As can be seen in FIG. 1d, the height of the handle 102a in this exemplary embodiment between the opposing sides shown in FIGS. 1b and 1c is constant along the length of the handle 102a.

Figure 1E:
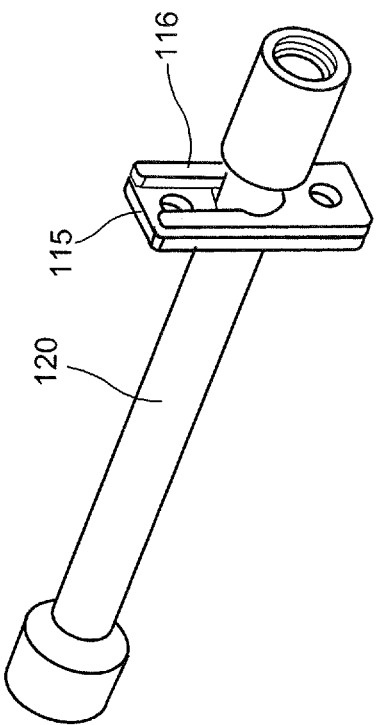
FIG. 1e shows a portion of a shaft of the driver of FIG. 1a and a clamp for transferring torque applied via a handle to the shaft, the clamp being in an open configuration, according to an embodiment of the present invention.
Figure 1F:
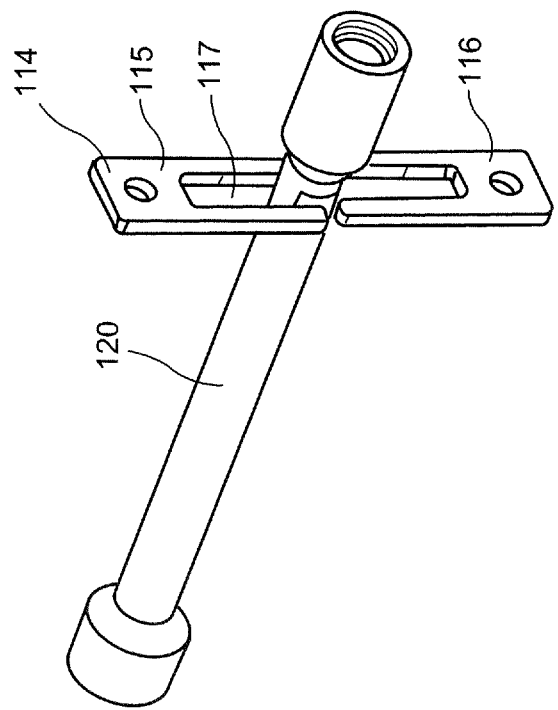
FIG. 1f shows the portion of the shaft and the clamp of FIG. 1e, where the clamp is in a locked configuration.
Figure 3:
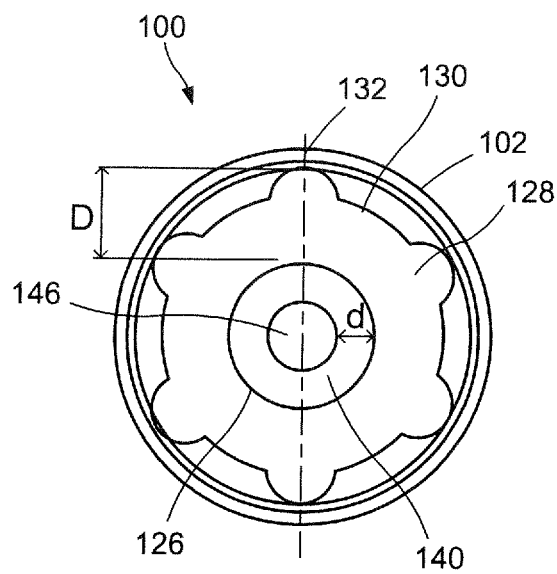
FIG. 3 shows a view from a distal end of the driver of FIG. 1a in a proximal direction.

The shaft 120 includes one or more clamps 114 located at or near the enlarged portion 110 of the handle 102 extending along a plane transverse to the longitudinal axis L1. The clamp 114 may include any suitable structure for clamping on to the shaft 120 and extending transverse to the longitudinal axis L1 such that rotation of the silicon molded handle 102 by a user transfers torque to the shaft 120. As shown in the embodiments of FIGS. 1e and 1f, the clamp 114 is placed onto the shaft 120 prior to molding over both the shaft 120 and the clamp 114 with an elastomeric molding to form the handle 120. The clamp 114 is movable between an open configuration, shown in FIG. 1e, and a locked configuration, shown in FIG. 1f. The clamp 114 comprises a first portion 115 and a second portion 116 slidably engaged with one another defining a slot 117 therebetween. In the open configuration shown in FIG. 1e, the slot 117 is suitably sized and shaped to slidably receive the shaft 120 therein. The first and seconds portions 115 and 116 are configured to move towards one another (as shown by the arrows in FIG. 1e) to the locked configuration shown in FIG. 1f to reduce the size of the slot 117 such that the slot 117 lockingly engages the shaft 120 by pushing the first and second portions 115, 116 towards each other to securely clamp against the exterior of the shaft 120. The handle 102 may further include additional surface features (not shown) configured to enhance a grip of the handle 102 by the user.

The distal end 124 of the shaft 120 forms a driving element 128 that is suitably sized and shaped to be inserted into a head portion 208 of the endcap 200. In particular, the driving element 128 is suitably sized and shaped to non-rotatably engage a recess 216 of the head portion 208 of the end cap 200. In one embodiment, the driving element 128 is suitably sized and shaped to non-rotatably engage the recess 216 so that manipulation of the handle 120 while the driving element 128 is engaged with the recess 216 drives the body portion 206 of the endcap 200 into the channel 16 of the intramedullary nail 10. The driving element 128 is configured to non-rotatably engage the head portion 208 of the endcap 200 such that rotation of the handle 102 transfers torque through the shaft 120 to the driving element 128. Torque applied to the handle 102 rotatably drives the endcap 200 into the channel 16 of the intramedullary nail 10.

The driving element 128 shown in FIG. 1a is in the shape of an elongated cylinder with a series of circumferentially spaced projections 132. As shown in FIG. 1a, the projections 132 are evenly spaced about the circumference of the cylinder. The projections 132 in this embodiment are rounded or curved and extend along a part of or an entire length of the driving element 128 defining therebetween longitudinal grooves 130 that extend along a part of or an entire length of the driving element 128. The projections 132 form protruding surface features to non-rotatably engage with the head portion 208 of the endcap 200. Alternatively, the driving element may have an elongated shape with a polygonal cross-section or a substantially polygonal cross-section, for example, a cross-section that is substantially hexagonal (e.g., a hex-key) in a plane orthogonal to a longitudinal axis L1 of the shaft 120.

The driver 100 further includes a retention pin 140 that extends through the shaft channel 126 from a proximal end 142 to a distal end 144 along the longitudinal axis L1. The retention pin 140 is coaxial with the shaft 120 along the longitudinal axis L1. The retention pin 140 is sized and shaped to be slidable and/or rotatable within the shaft channel 126. In some embodiments, the retention pin 140 is sized and shaped to correspond to the size and shape of the shaft channel 126, for example, a cylindrical shape. The cylindrical shape of the retention pin 140 may have a cross-sectional outer diameter from about 3 mm to about 4 mm and inner diameter of about 1.7 mm to about 2.1 mm, in a plane orthogonal to the longitudinal axis L1. The retention pin 140 defines a lumen 146 extending longitudinally from the proximal end 142 to the distal end 144 along the longitudinal axis L1. The lumen 146 of this embodiment is co-axial with the retention pin 140 and defines a thickness d (e.g., shown in FIGS. 2 and 3) from an exterior surface of the retention pin 140 to an interior surface of the lumen 146. In some embodiments, the thickness d of the retention pin is from about 0.45 mm to about 1.15 mm.

As shown in FIG. 1a, the proximal end 142 of the retention pin 140 extends proximally beyond the proximal end 122 of the shaft 120. The retention pin 140 may be slidably movable or longitudinally fixed with in the shaft channel 126. In some embodiments, the distal end 144 of the retention pin 140 extends distally beyond the distal end 124 of the shaft 120. In other embodiments, the distal end 144 of the retention pin 140 is slidably movable between a retracted configuration in which the distal end 144 is positioned within the shaft channel 126 and an extended configuration in which the retention pin 140 extends distally beyond the distal end 124 of the shaft 120 so that it may engage with the head portion 208 of the endcap 200. The distal end 144 of the retention pin 140 comprises a surface feature configured to reversibly lock the shaft 120 to the head portion 208 of the endcap 200. In particular, the surface feature is suitably sized and shaped to reversibly engage a corresponding feature within the head portion 208 of the endcap 200. When the surface feature is engaged with the head portion 208, the endcap 200 is lockingly coupled to the distal end 144 of the retention pin 140. For example, the surface feature in this embodiment comprises threading 146 for engaging corresponding threading 220 in the head portion 208 of the endcap 200.

The driver 100 further includes a knob 160 rotatably connected to the proximal end 122 of the shaft 120. Rotation of the knob 160 about the longitudinal axis L1 rotates the retention pin 140 to lock and unlock the retention pin 140 from the head portion 208 of the endcap 200. The knob 160, in this embodiment, is rotatably connected to the shaft 120 via an axle mechanism 162 fixedly attached to a proximal portion of the shaft 120. As shown in FIG. 1a, the axle mechanism 162 is inserted into a proximal portion of the shaft channel 126 and rotatably fixed therein. The axle mechanism 162 includes an axle channel 164 extending longitudinally through the axle mechanism 162 to receive the retention pin 140. The axle mechanism 162 is rotatably connected to the knob 160. The knob 160 is also non-rotatably connected to a proximal end 142 of the retention pin 140 such that rotation of the knob 160 in a desired direction about the longitudinal axis L1 rotates the retention pin 140 in the same direction.

For example, FIG. 1a shows that the proximal end 142 of the retention pin 140 is embedded within the knob 160. The knob 160 further includes a knob channel 166 aligned with the lumen 146 of the retention pin 140 to permit a guidewire 300 to extend through the knob channel 162 into the lumen 146 of the retention pin 140. The knob 160 may have any suitable size and shape for being held between the fingertips of a user's hand to facilitate manual manipulation of the knob 160. Preferably, the knob 160 is suitably sized and shaped to provide an ergonomic shape for a user to pinch between an index finger and a thumb to manipulate, or rotate, the knob 160 by hand. The knob 160 may include additional surface features (not shown) configured to enhance a grip of the knob 160 by the fingertips of a user as would be understood by those skilled in the art.

Figure 4:
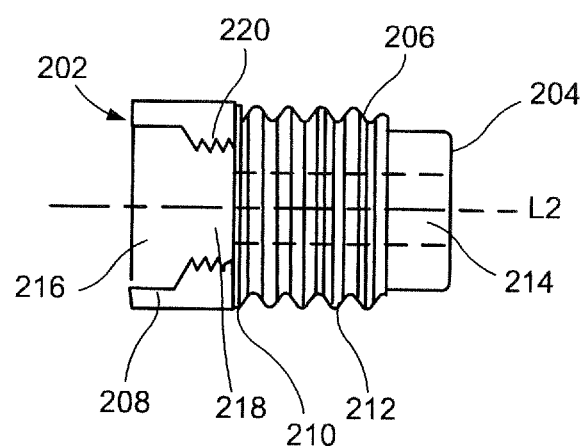
FIG. 4 shows a side view of an endcap according to an embodiment of the present invention.

FIG. 4 shows an endcap 200 configured to be inserted into a proximal opening 14 of a channel 16 in the intramedullary nail 10 to close the proximal opening 14 of the channel 16 to prevent bone ingrowth into the channel 16. The endcap 200 is configured to reversibly engage and disengage an interior surface of the channel 16 in the intramedullary nail 10 via any suitable engagement structure, such as, for example, threading 212 configured to engage corresponding threading within the interior surface of the channel 16. The endcap 200 extends from a proximal end 202 to a distal end 204 and includes a body portion 206 and a head portion 208 proximal of the body portion 206. The body portion 206 extends from a proximal end 210 thereof to the distal end 204 of the endcap 100. The head portion 208 extends proximally from the proximal end 210 of the body portion 206. The endcap 200 further includes a lumen 214 extending from the proximal end 202 to the distal end 204 along a longitudinal axis L2 thereof. The lumen 214 being configured to receive a guide wire 300 therethrough.

The body portion 206 of the endcap 200 is configured to be inserted into and engage a channel 16 of an intramedullary nail 10. In particular, the distal end 204 is suitably sized and shaped to be inserted into a proximal opening 14 of a channel 16 in the intramedullary nail 10 and fixedly engage an interior of the channel 16 of the intramedullary nail 10. The body portion 106 may include any suitable engagement structure, e.g., threading 212, snap fasteners, adhesives or screws to attach endcap 200 to the channel 16 of the intramedullary nail 10. In some embodiments, the body portion 206 includes at least a portion having a threading 212 configured to threadedly engage the interior of the channel 16 of the intramedullary nail 10. The threading 212 may extend along a part of or an entire longitudinal length of the body portion 206. The threading 212 is configured to mate with corresponding threading in the interior of the channel 16 of the intramedullary nail 10 as the endcap 200 is driven into the channel 16 of the intramedullary nail 10, to secure the endcap 200 to the proximal end 12 of the intramedullary nail 10.

The head portion 208 of the endcap 200 comprises a recess 216 for engaging the driver 100, in particular, the driving element 128 of the shaft 120. For example, the recess 216 has a size and shape corresponding to that of the driving element 128 for receiving and engaging the driving element 128. The recess 216 is suitably sized and shaped to engage the driving element 128 so that manipulation of the driver 100 while the driving element 128 is engaged with the recess 216 drives the endcap 200 into or out of the channel 16 of the intramedullary nail 10. More particularly, the recess 216 is configured to non-rotatably engage the driving element 128 such that rotation of the shaft 120 transfers torque from the shaft 120 through the head portion 208 to drive the body portion 206 of the endcap 200 into the channel 16.

The recess 216 also includes a corresponding surface feature suitably sized and shaped to reversibly engage the surface feature at the distal end 144 of the retention pin 140 such that the head portion 208 of the endcap 200 reversibly locks to the shaft 120. For example, the recess 216 includes an indentation 218 extending distally from the recess 216 along the longitudinal axis L2. In some embodiments, the indentation 218 is a cylindrical channel having corresponding threading 220 configured to mate with the threading 146 at the distal end 144 of the retention pin 140 as the retention pin 140 extends distally past the distal end 124 of the shaft 120 and is driven into the indentation 218 to secure the endcap 200 to the distal end 144 of the retention pin 140. The indentation 218 is suitably sized and shaped to engage the distal end 144 of the retention pin 140 so that rotation of the knob 160 rotates the retention pin 140 to drive the threading 146 located at the distal end 144 of the retention pin 140 to lockingly engage the corresponding threading 220.

When the threading 146 of the retention pin 140 locks to the corresponding threading 220 of head portion 208, the endcap 200 is lockingly coupled to the distal end 144 of the retention pin 140 so that manipulation of the shaft 120 does not accidentally disengage the head portion 208 from the driver 100. This minimizes the risk that the endcap 200 will be accidentally dropped during implantation. The threading 146 of the retention pin 140 is suitably sized and shaped to disengage from the corresponding threading 220 by rotating the knob 160 in a reverse direction to rotatably withdraw the distal end 144 of the retention pin 140 from the indentation 218 to unlock the retention pin 140 from the head portion 208 after the endcap 200 has been driven to a desired position in the channel 16 of the intramedullary nail 10.

Figure 5:
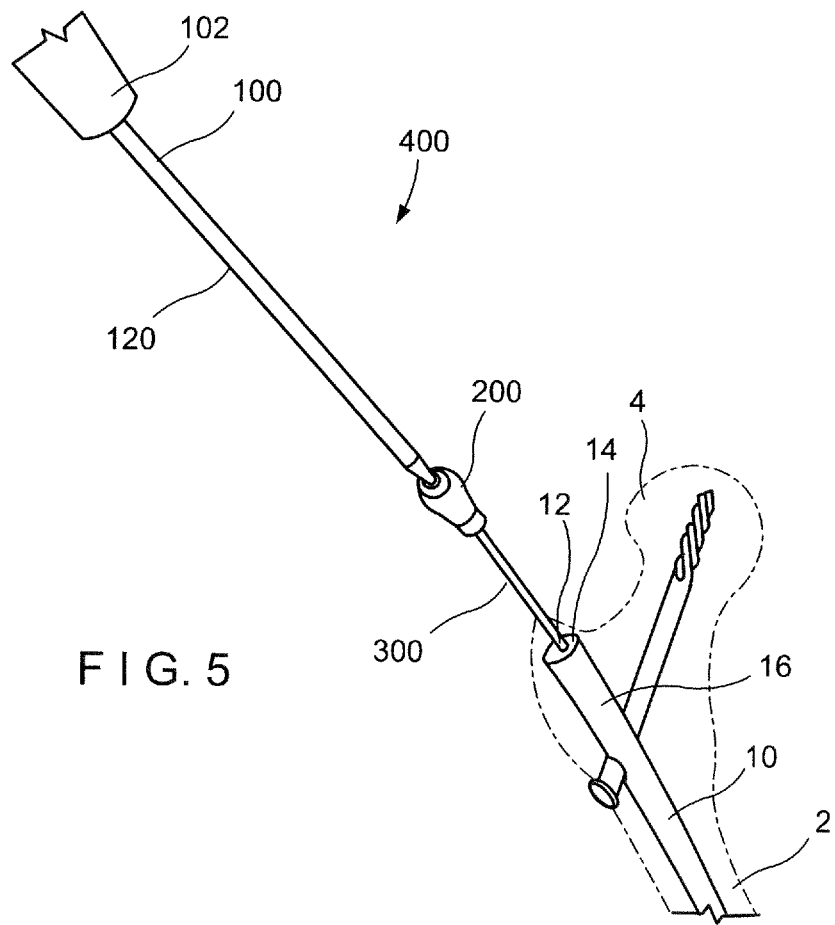
FIG. 5 shows a perspective view a system for a femur according to an embodiment of the present invention including the driver of FIG. 1a engaging the endcap of FIG. 4 and guiding the endcap over a guidewire for insertion into a proximal opening of a channel of an intramedullary nail.

The driver 100 and the endcap 200 as described above may be provided along with a guidewire 300 as part of a system 400 for engaging a proximal end of an intramedullary nail 16. As can be seen in an exemplary embodiment shown in FIG. 5, the endcap 200 may be installed at the proximal end 12 of the intramedullary nail 10 by inserting a guidewire 300 into the channel 16 of the intramedullary nail 10 and sliding the endcap 200 over the guidewire 300 via lumen 214 towards a desired position over the proximal end 12 of the intramedullary nail 10. The driver 100 is also configured to receive the guidewire 300 therethrough and slide into position to engage the head portion 208 of the endcap 200. Specifically, when the system is in use, the guidewire 300 is slidably inserted from the proximal end of the driver 100 through the knob channel 162 and the lumen 146 to the distal end 144 of the retention pin 140 and also through the recess 216 and lumen 214 of the endcap 200. The driver 100 and the endcap 200 are slid into position along the guidewire 300 to engage the driver 100 with the endcap 200 such that the longitudinal axis L1 of the driver 100 and the longitudinal axis L2 of the endcap 200 are substantially aligned, or aligned within the predetermined angular range of tolerance.

Once the driver 100 has been inserted into the recess 216 of the endcap 200 to engage the head portion 208, the knob 160 is rotated to drive the threading 146 of the retention pin 140 into the corresponding threading 220 of the head portion 208 to lockingly engage the distal end 144 of the retention pin 140 to the endcap 200. Once the endcap 200 has been securely locked to the driver 100, manipulation (e.g., rotation) of the handle 102 translates applied forces and/or torque to the endcap 200. In particular, the driver 100 may be manipulated to drive the body portion 206 of the endcap 200 into the channel 16 of the intramedullary nail 10. The endcap 200 may be driven into the channel 16 of the intramedullary nail 10 such that a portion of or an entire longitudinal length of the body portion 206 of the endcap 200 lies within the channel 16 when it is fully inserted. In some embodiments, only a portion of the length of the body portion 206 is inserted and engaged with the channel 16 such that the endcap 200 provides a proximal extension to the intramedullary nail 10.

In certain embodiments, the shaft 102 and/or the retention pin 140 are formed of a material having a rigidity sufficient to resist deformation of the shaft during use. For example, the shaft 102 has a rigidity sufficient to resist twisting and/or bending upon application of forces and/or torque of an expected magnitude via the handle 102 to drive the body portion 206 of the endcap 200 into the channel 16 of the intramedullary nail 10. In addition or in the alternative, the retention pin 140 has a rigidity sufficient to resist twisting and/or bending when the knob 160 is rotated to drive the threading 146 of the retention pin 140 into the corresponding threading 220 of the head portion 206. The rigidity of the shaft 102 and/or the retention pin 140 resists yielding to applied forces and/or torque such that the distal end 124 of the shaft 102 and/or the distal end 144 of the retention pin 140 is easily substantially aligned to engage with the head portion 208 of the endcap 200 when the device is in use, in particular, to engage the threading 146 of the retention pin 140 with the corresponding threading 220 of the head portion 208. The shaft 102 and/or retention pin 140 may be formed from any suitable material that provides the desired rigidity, such as, for example, stainless steel (e.g., 1.4301 stainless steel, 1.4542 stainless steel, Custom 465 stainless steel, 1.4123 stainless steel, or 1.4109 stainless steel.)

Figure 6:
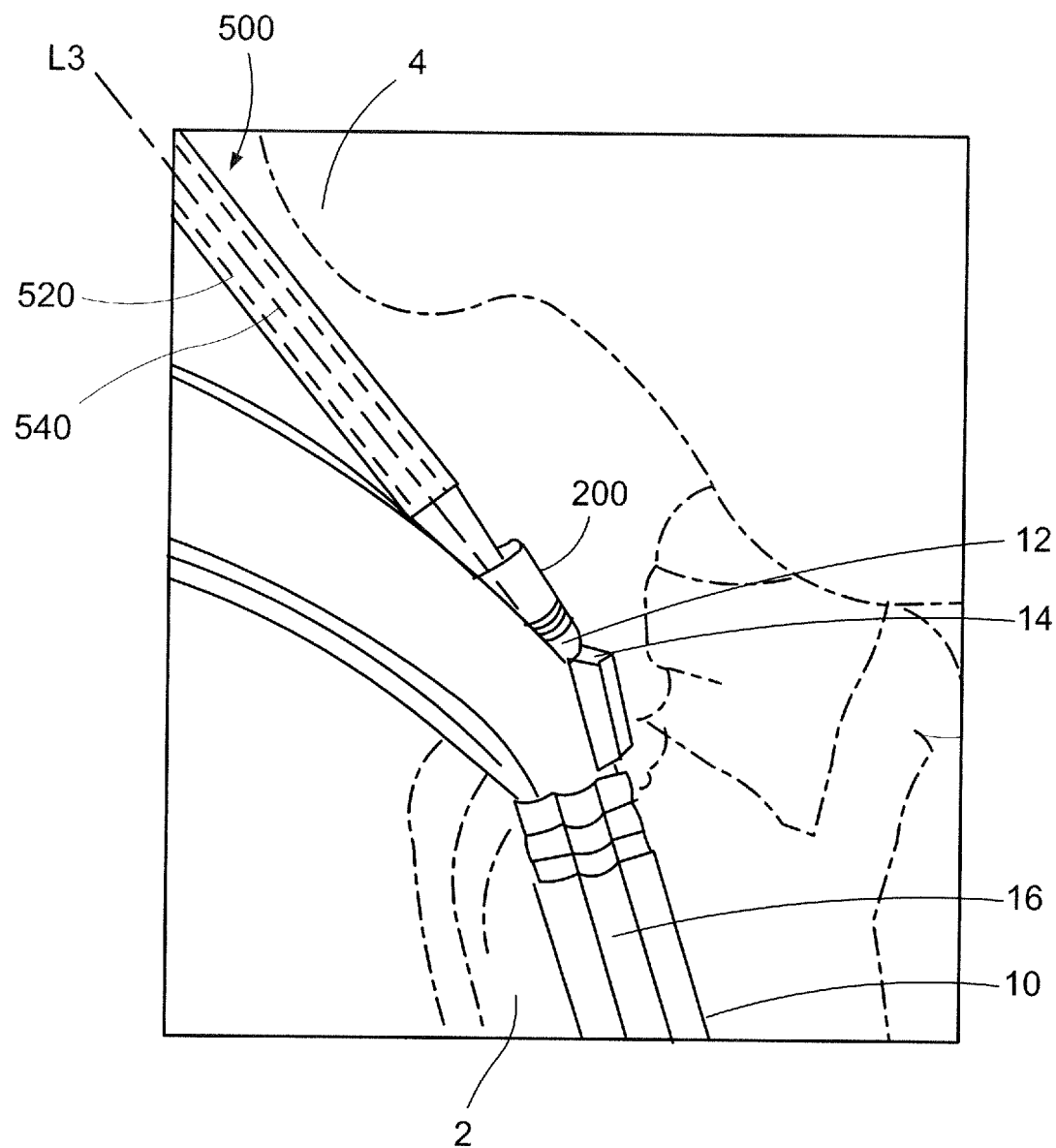
FIG. 6 shows a perspective view of a system for a femur according to an alternative embodiment of a driver engaging the endcap of FIG. 4 for insertion into a proximal opening of a channel of an intramedullary nail in a femur.
Figure 7:
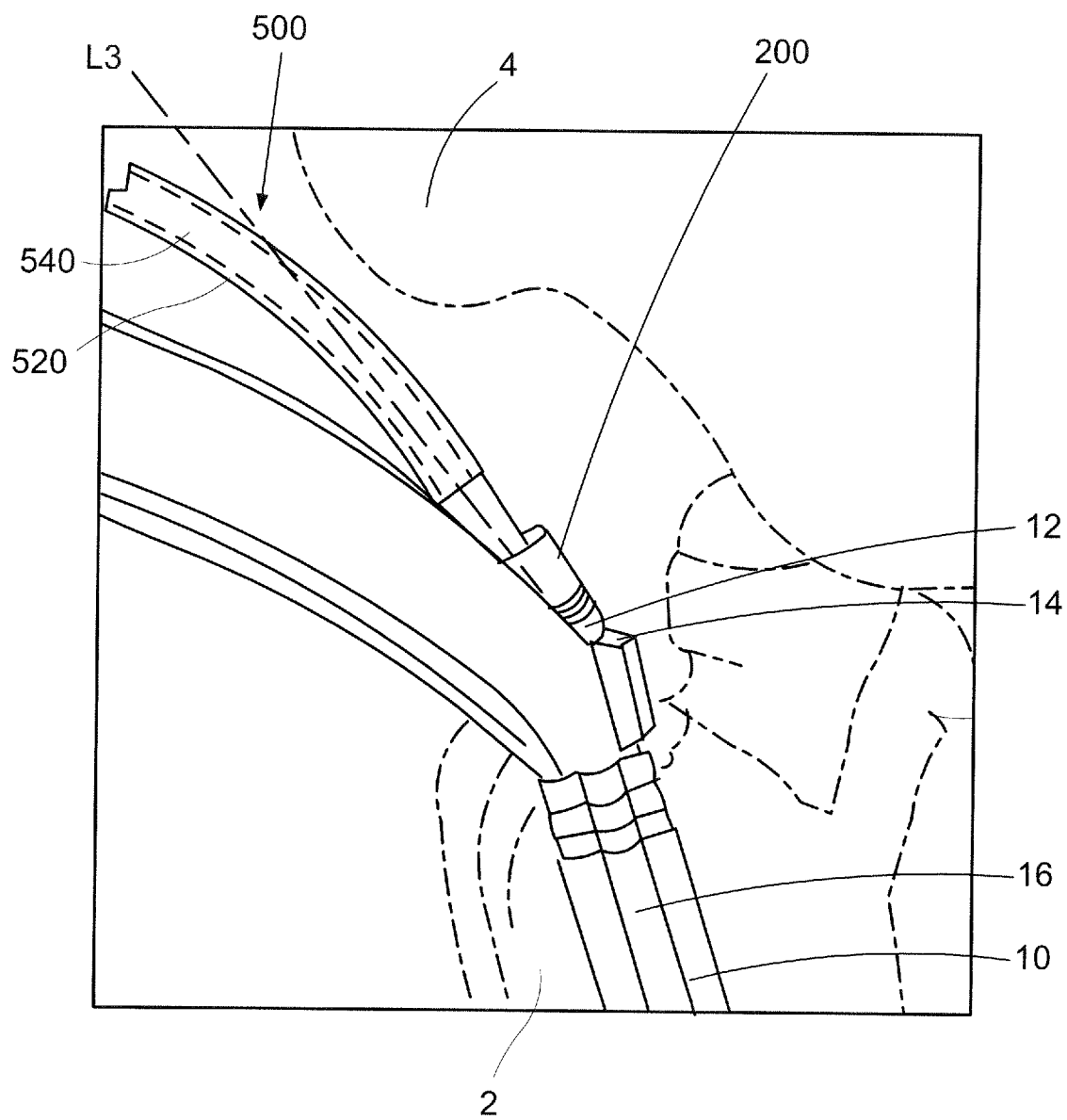
FIG. 7 shows a perspective view of the system of FIG. 6 with the driver in an elastically deformed configuration extending along a curved path away from a longitudinal axis of the driver.

In other embodiments, a driver 500 may comprise a shaft 520 and a retention pin 540 that are flexible and reversibly movable between a relaxed configuration and a deformed configuration. The driver 500 shown in FIGS. 6 and 7 is substantially similar to the driver 100 of FIGS. 1a-c and 3, with like elements referenced with like reference numerals. In this alternative embodiment, the shaft 520 and the retention pin 520 are movable between a relaxed configuration (shown in FIG. 6) in which the shaft 520 and the retention pin 540 lie along the longitudinal axis L3, and a deformed configuration (shown in FIG. 7) in which the shaft 520 and the retention pin 540 are elastically deformed to extend along a curved path away from the longitudinal axis L3 to the endcap 200. This allows a user to manipulate the endcap 200 in the same manner described above even when the particular anatomy of a patient or the geometry of the surgical approach render it difficult or impossible to obtain a straight line of approach of the driver 500 to the end cap 200.

The shaft 520 and the retention pin 540 of this embodiment may be deformed when the device 500 is used to insert the endcap 200 into an intramedullary nail 10 for fixation of a femur 2. The shaft 520 and the retention pin 540 may be deformed upon application of force to push the shaft 520 and the retention pin 540 to bend along a curved path, for example, for circumventing the iliac crest 4 during use. When the force is removed from the shaft 520 and the retention pin 540, the shaft 520 and the retention pin 540 return to the relaxed configuration. In one example, the flexibility of the shaft 102 and/or the retention pin 140 varies along a length thereof. For example, the shaft 102 and/or retention pin 140 may comprise a plurality of regions, each region having a different degree of flexibility.

Figure 8A:
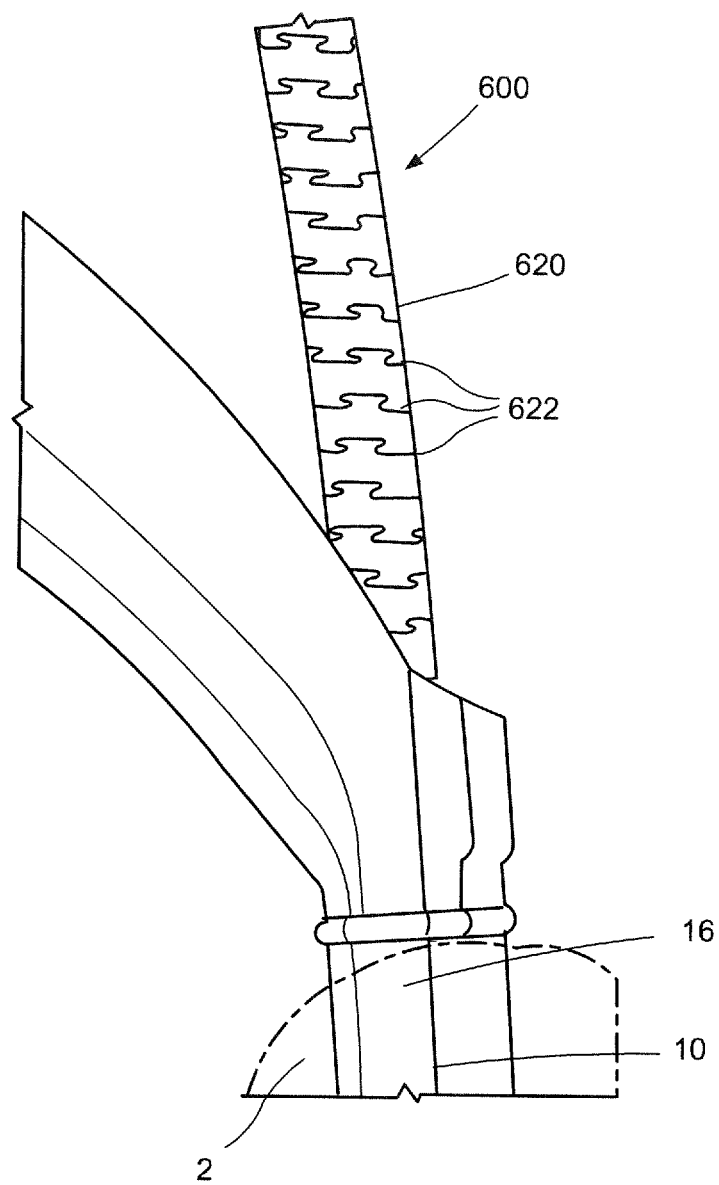
FIG. 8a shows a perspective view of an embodiment of a flexible driver engaging the endcap of FIG. 4.
Figure 8B:
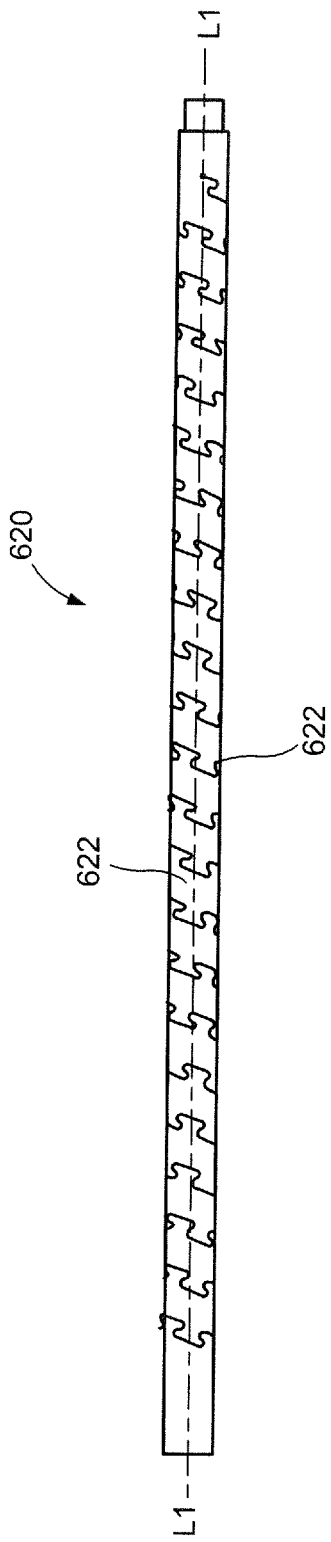
FIG. 8b shows a side view of a shaft of the flexible driver of FIG. 8a having a plurality of grooves extending along a length of the shaft for imparting increased flexibility to the shaft.
Figure 8D:
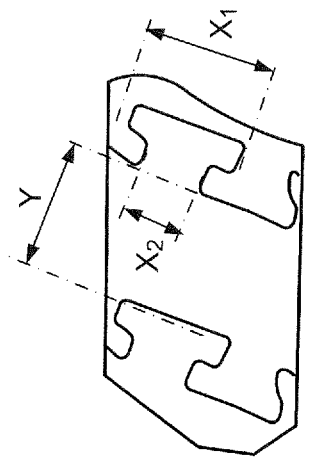
FIG. 8d shows another detailed view of a portion of the shaft of FIG. 8b having the plurality of grooves.
Figure 8C:
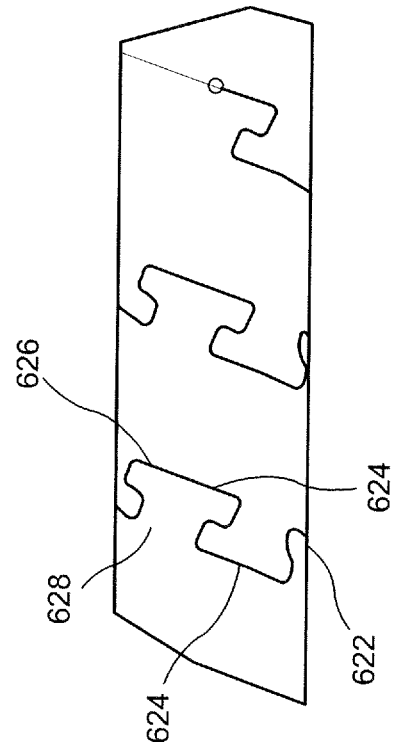
FIG. 8c shows a detailed view of a portion of the shaft of FIG. 8b having a plurality of grooves.

In one exemplary embodiment, the driver 600 may comprise a shaft 620 that includes surface features that increase flexibility of the shaft 620 such that the shaft 620 is movable between a relaxed configuration and a deformed configuration. The driver 600 shown in FIG. 8*a* is substantially similar to the driver 100 of FIGS. 1*a-c* and 3, with like elements referenced with like reference numerals. In this exemplary embodiment, the shaft 620 includes aligned groove(s) 622 wrapping around an external surface of the shaft 620 and extending along at least a portion of the shaft 620 to impart increased flexibility to the shaft 620. For example, the grooves 622 may extend along a length of the shaft 620 (e.g., 200 mm of the shaft 620) such that the shaft 620 is sufficiently flexible for bending up to 45° away from the longitudinal axis L1, as shown in FIG. 8*b*. As shown in FIGS. 8*b* and 8*c*, the grooves 622 may comprise laser cut windings wrapping around an external surface of the shaft 620. The laser cut windings may be angled to a plane along the longitudinal axis L1 and substantially parallel to one another.

In one exemplary embodiment shown in FIG. 8*c*, the grooves 622 extend at a 72° angle from the plane along the longitudinal axis L1. The grooves 622 may have any suitable shape and pattern. As shown in FIGS. 8*b*-8*d*, the grooves 622 are cut in an interlocking pattern having a wing 624 extending transverse to the angle of the windings, the wing 624 comprising a widened portion 626 and a narrow neck portion 628. The narrow neck portion 628 configured to interlock with the widened portion 626 of the next wing 624 in the interlocking pattern. The widened portion 626 has a width $x_1$ and the narrow neck portion 628 has a width $x_2$ where $x_1 > x_2$. For example, the widened portion 626 has a width $x_1$ from about 5.1 mm to 5.5 mm and the narrow neck portion 628 has a width $x_2$ a width from about 2.6 mm to 3.0 mm. The windings may be spaced apart by a distance y between each of the windings, as shown in FIG. 8*d*. The distance y is, for example, from about 2.6 mm to about 5.2 mm. In one particular embodiment (not shown), the shaft 620 may have a plurality of regions, each region having a different degree of flexibility provided by a different distance y between the windings, where a smaller distance y provides an increase in flexibility to the shaft 620.

The shaft 520, 620 and/or retention pin 540 may be formed from any material that deforms when a predetermined level of force is applied to the material and resumes its original shape once the external force is removed. In one embodiment, the shaft 620 is formed from a metal, in particular, a biocompatible stainless steel (e.g., 1.4542 stainless steel), having aligned groove(s) 622 extending along at least a portion of the shaft 620 to impart increased flexibility to the shaft 620, as discussed above. In another embodiment, the shaft 520, 620 may be formed from an elastic material. The elastic material may be a memory metal alloy, for example, nitinol. In particular, the elastic material may consist of a nickel-titanium alloy, in which 45%<Ni<55%, 45% Ti<55% and x+y=100%. Such a material is particularly biocompatible and highly elastic. The memory metal alloy may have a transition temperature of more than about 50° C. and, more preferably, more than about 80° C. In another embodiment, the transition temperature may be more than about 100° C. and, preferably, more than about 120° C.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

What is claimed is:

1. A driver for engaging an endcap of an intramedullary nail, comprising:
   a handle extending along a longitudinal axis of the driver from a proximal end to a distal end and having a handle channel extending longitudinally therethrough, wherein the handle is formed from an elastomeric material;
   a shaft extending through the handle channel from a proximal end to a distal end along the longitudinal axis having a shaft channel extending longitudinally therethrough, the distal end of the shaft extending distally from the handle, the distal end of the shaft forming a driving element configured to be inserted into a head portion of the endcap, wherein the shaft is rotatably fixed within the handle channel such that rotation of the handle transfers torque through the shaft to the driving element, the driving element being configured to non-rotatably engage the endcap so that torque applied to the handle rotatably drives the endcap to couple the endcap to the intramedullary nail, and wherein the shaft is rotatably fixed within the handle channel via a clamp extending along a plane transverse to the longitudinal axis of the handle and fixedly clamped onto the shaft for transferring torque applied to the handle through the clamp to the shaft; and
   a retention pin slidably received in the shaft channel and extending from a proximal end to a distal end along the longitudinal axis, the distal end of the retention pin configured to reversibly lock the shaft to the head portion of the endcap.

2. The driver of claim 1, further comprising:
   a knob rotatably connected to the proximal end of the shaft, rotation of the knob about the longitudinal axis rotating the retention pin to lock and unlock from the head portion of the endcap.

3. The driver of claim 2, wherein the distal end of the retention pin comprises threading configured to threadedly engage a corresponding threading in the head portion of the endcap.

4. The driver of claim 1, wherein the retention pin includes a lumen extending longitudinally therethrough, the lumen sized and shaped to slidably receive a guidewire therethrough.

5. The driver of claim 1, wherein the distal end of the retention pin extends distally beyond the distal end of the shaft.

6. The driver of claim 1, wherein the shaft is formed of a material having a rigidity sufficient to resist deformation of the shaft during use.

7. The driver of claim 1, wherein the shaft and the retention pin are flexible and reversibly movable between a relaxed configuration in which the shaft and the retention pin lie along the longitudinal axis, and a deformed configuration in which the shaft and the retention pin are elastically deformed to extend along a curved path to the endcap.

8. The driver of claim 7, wherein the flexibility of the shaft varies along a length of the shaft.

9. The driver of claim 7, wherein the shaft comprises a plurality of aligned grooves wrapping around an external surface of the shaft for imparting flexibility to the shaft.

10. The driver of claim 1, wherein a wall of the retention pin has a thickness from about 0.45 mm to about 1.15 mm.

11. The driver of claim 1, wherein the retention pin has an outer diameter from about 3 mm to about 4 mm.

12. The driver of claim 11, further configured to receive a guidewire having a diameter from about 1.6 mm to about 2.0 mm.

13. A system for engaging a proximal end of an intramedullary nail, comprising:
  (i) a driver comprising
    a handle extending along a longitudinal axis of the driver from a proximal end to a distal end and having a handle channel extending longitudinally therethrough, wherein the handle is formed from an elastomeric material,
    a shaft extending through the handle channel from a proximal end to a distal end along the longitudinal axis having a shaft channel extending longitudinally therethrough, the distal end of the shaft extending distally from the handle, the distal end of the shaft forming a driving element, wherein the shaft is rotatably fixed within the handle channel such that rotation of the handle transfers torque through the shaft to the driving element, the driving element being configured to non-rotatably engage the endcap so that torque applied to the handle rotatable drives the endcap to couple the endcap to the intramedullary nail, and wherein the shaft is rotatably fixed within the handle channel via a clamp extending along a plane transverse to the longitudinal axis of the handle and fixedly clamped onto the shaft for transferring torque applied to the handle through the clamp to the shaft, and
    a retention pin slidably received in the shaft channel and extending from a proximal end to a distal end along the longitudinal axis, the distal end of the retention pin comprises threading, the retention pin including a lumen extending longitudinally therethrough;
  (ii) an endcap having a lumen extending therethrough comprising
    a body configured to engage a channel of the intramedullary nail, and
    a head portion configured to receive the driving element therein and to reversibly lock the head portion to the shaft, the head portion comprising threading configured to threadedly engage a corresponding threading of the retaining pin; and
  (iii) a guidewire slidably inserted through the lumen of the retention pin and the lumen of the endcap to align the driving element to the head portion of the endcap.

14. The system of claim 13, wherein the distal end of the retention pin extends distally beyond the distal end of the shaft.

15. The system of claim 13, wherein the shaft is formed of a material having a rigidity sufficient to resist deformation of the shaft during use.

16. The system of claim 13, wherein the shaft and the retention pin are flexible and reversibly movable between a relaxed configuration in which the shaft and the retention pin lie along the longitudinal axis, and a deformed configuration in which the shaft and the retention pin are elastically deformed to extend along a curved path to the endeap.

* * * * *